United States Patent [19]
Griffiths Lawson

[11] Patent Number: 5,952,471
[45] Date of Patent: Sep. 14, 1999

[54] ANTIBODY THAT BINDS TO CLUSTER W-4 POLYPEPTIDE OF HUMAN SMALL CELL LUNG CARCINOMA CELLS

[75] Inventor: Alastair David Griffiths Lawson, Arlesford, United Kingdom

[73] Assignee: Celltech Therapeutics Limited, United Kingdom

[21] Appl. No.: 08/776,694

[22] PCT Filed: Jul. 31, 1995

[86] PCT No.: PCT/GB95/01795

§ 371 Date: Feb. 3, 1997

§ 102(e) Date: Feb. 3, 1997

[87] PCT Pub. No.: WO96/04312

PCT Pub. Date: Feb. 15, 1996

[30] Foreign Application Priority Data

Aug. 1, 1994 [GB] United Kingdom .................... 9415492

[51] Int. Cl.⁶ .................................................. C07K 16/00
[52] U.S. Cl. .................................... 530/387.1; 530/387.7; 530/387.9; 530/391.1
[58] Field of Search ................ 530/350, 387.1, 530/387.7, 387.9, 391.1; 424/130.1, 178.1; 514/2; 435/69.1

[56] References Cited

FOREIGN PATENT DOCUMENTS

| | | |
|---|---|---|
| 147118 | 7/1985 | European Pat. Off. . |
| 323802 | 7/1989 | European Pat. Off. . |
| 0356397 | 2/1990 | European Pat. Off. . |
| 356397 | 2/1990 | European Pat. Off. . |
| 9317715 | 9/1993 | WIPO . |

OTHER PUBLICATIONS

Hiskey et al. (1967) J. Am. Chem. Soc. 89:437–41.
Jackson et al. (1992) Cancer Res. 52:5264–70.
Weber et al. (1993) Clin. Exp. Immunol. 92:279–85.
Yamamura (1993) Cancer Res. 53:423–8.
Kimmel et al J. Neurosurg. 66:161–171, 1987.
Jackson et al (Can. Res. 1992, 52: 5264–5270).
Weber et al (Clin. Exp. Immunol, 1993, 93: 279–285).

*Primary Examiner*—Paula K. Hutzell
*Assistant Examiner*—Susan Ungar
*Attorney, Agent, or Firm*—Klauber & Jackson

[57] ABSTRACT

Binding agents, such as antibodies, are described which selectively bind to the cluster-w4 polypeptide of human small cell lung carcinoma cells at a site located at and around valine-57 of the cluster-w4 polypeptide. The binding agents, either alone or linked to a reporter or effector molecule are of use in the diagnosis or treatment of human small cell lung carcinoma. Also described are peptides $(A)_m\text{-}(T)_n\text{-}(T)_o\text{-}(K)_p\text{-}V\text{-}(A)_q\text{-}(G)_r\text{-}(G)_s\text{-}(A)_t\text{-}(L)_u$ having at least one of the core structures K-V-A, T-K-V, or V-A-G for use in the identification and/or preparation of binding agents according to the invention, as diagnostic reagents, or as immunostimulants.

5 Claims, 3 Drawing Sheets

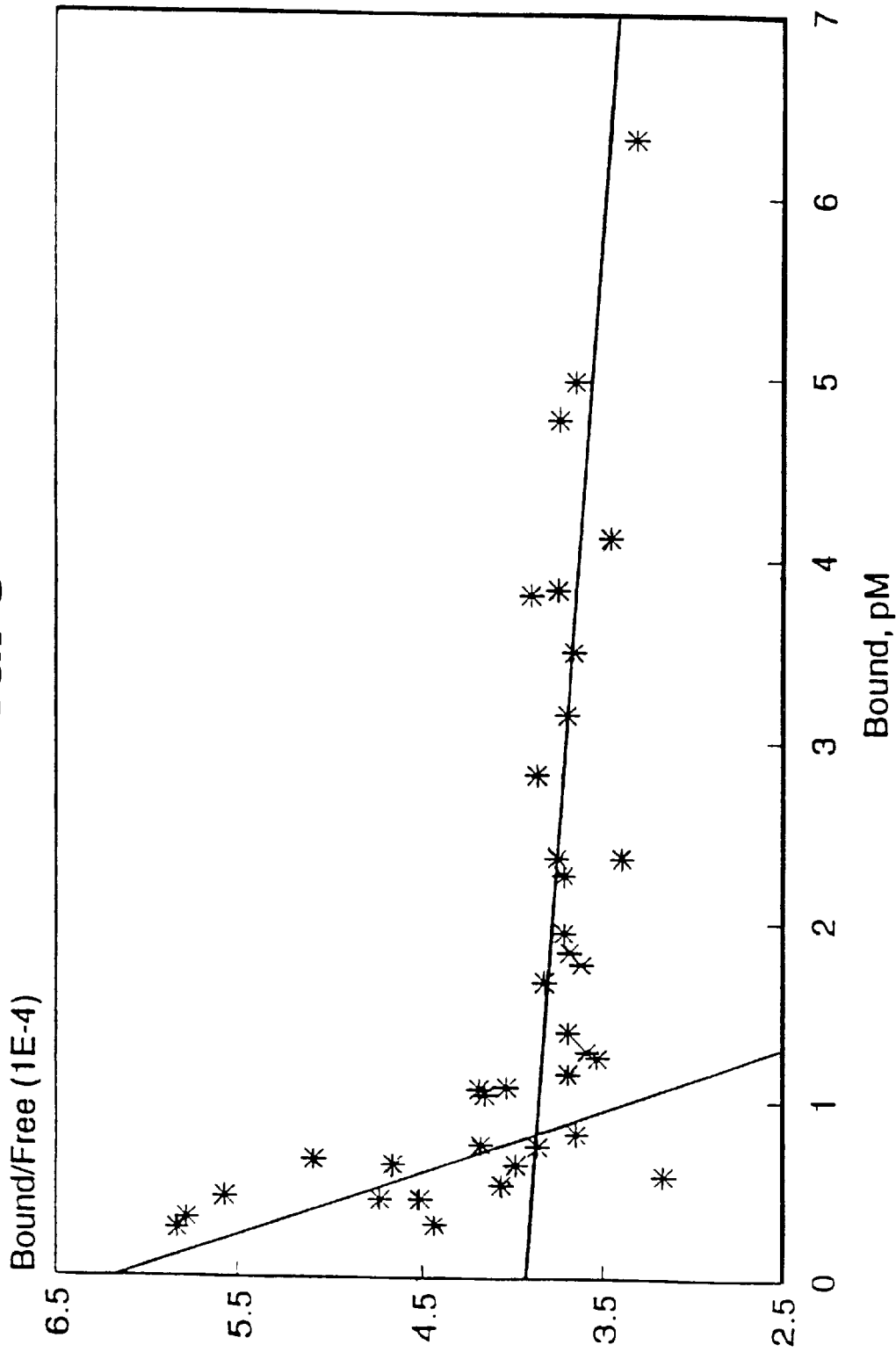

ANTIBODY THAT BINDS TO CLUSTER W-4 POLYPEPTIDE OF HUMAN SMALL CELL LUNG CARCINOMA CELLS

This invention relates to peptides and derivatives thereof, to binding agents, including antibodies, which bind selectively to the peptides and to the use of the peptides and binding agents in diagnosis and therapy.

Lung cancer is a leading cause of death in many countries. The disease can be divided into Small Cell Lung Carcinoma (SCLC) and Non-SCLC [Yesner, R., New Engl. J. Med. (1985) 312, 652–653]. SCLC comprises 25% of all newly diagnosed lung cancer cases and is characterised by a high metastatic capacity, a high proliferation rate and initially a high sensitivity to chemo- or radiotherapy. Despite good initial response to chemo- or radiotherapy, almost all of the responding patients relapse within one to two years with therapy resistant recurrences. As a result, five-year survival is extremely low [Ianuzzi, M. C., and Scoggin C. H., Am. Rev. Respir. Dis. (1986), 134, 594–608]. There is therefore a need for improved methods of diagnosis and treatment of SCLC.

Antibody-mediated diagnosis and therapy of SCLC is a potentially attractive solution, and in recent years a large number of monoclonal antibodies have been generated against surface antigens expressed on small cell lung carcinoma cells. Many of these antibodies have been divided into fifteen main clusters of reactivity, five of which define distinct glycoprotein antigens [The Third International Meeting on Lung Antigens, Zurich, 1993].

It has been suggested that one of these glycoprotein antigens, the so-called cluster-w4 antigen, might be a promising target for antibody-mediated therapy of SCLC [Jackson, D., et al, Cancer Res. (1992), 52, 5264–5270]. However, this antigen has been shown to have the same biochemical properties as the leukocyte activation molecule CD24, found on the surfaces of human B cells and to have an identical primary sequence, except for a single valine-alanine substitution at position 57 on a proportion of the molecules [Jackson, D., et al ibid.]. Furthermore, the antigens have also been shown to be serologically identical using existing CD24 and cluster-w4 monoclonal antibodies, many of which have been demonstrated to recognise the short sequence leucine-alanine-proline (LAP) of the protein core of the CD24/cluster-w4 antigen [Weber, E., et al, Clin. Exp. Immunol. (1993), 93, 279–285].

The inability of existing antibodies to distinguish between the SCLC cluster-w4 antigen and leukocyte CD24 raises the question of whether these antibodies can ever be successfully used in diagnosis and therapy to differentiate between normal and tumour tissue. What is needed is an antibody which can recognise an epitope on the SCLC cluster-w4 antigen, but which does not cross-react with leukocyte CD24 antigen.

BRIEF DESCRIPTION OF THE DRAWINGS

FIG. 3 is a Scatchard Plot showing the binding of rat monoclonal antibody 9A6 to the human small cell lung carcinoma cell line H128.

Figure 1:
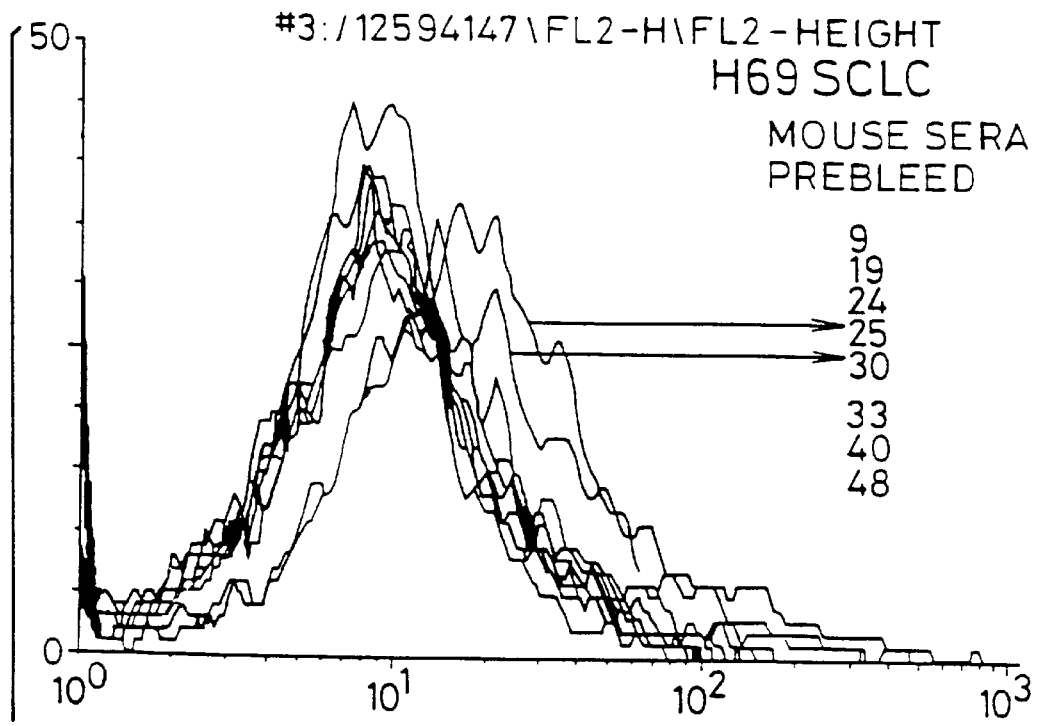
FIG. 1 is a FACScan analysis illustrating the differential binding of antibodies in mice sera (arrowed) to the human small cell lung carcinoma cell line H69 and the human erythroleukemic cell line K562.
Figure 1:
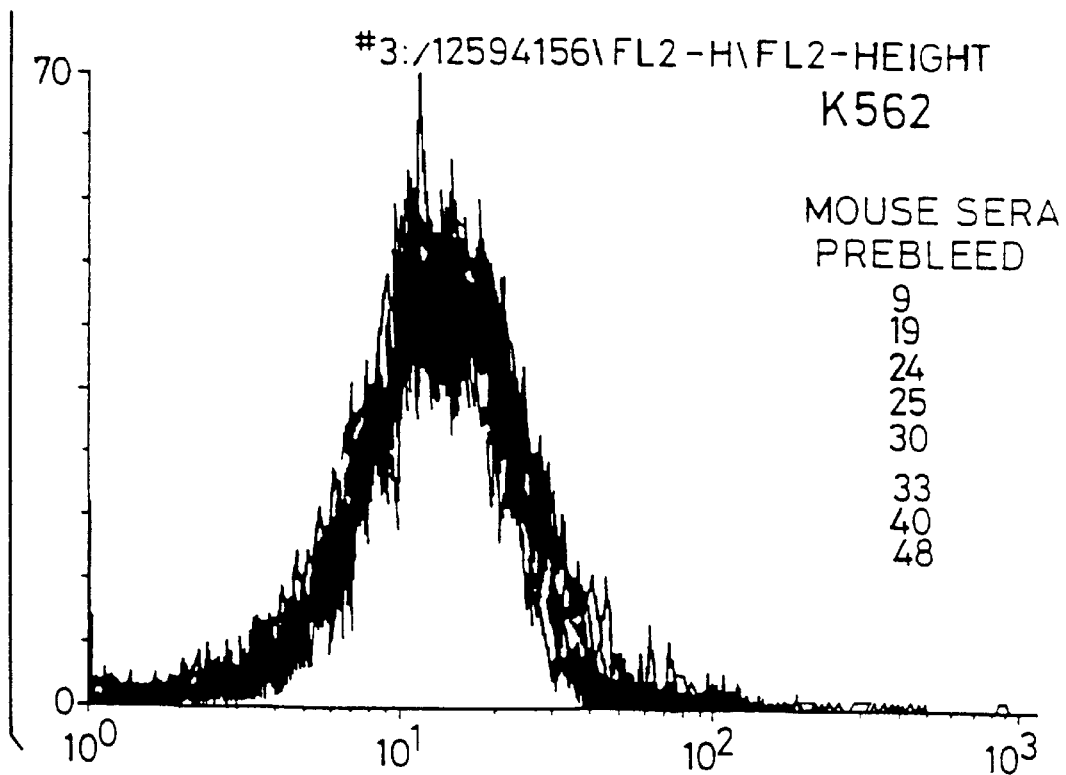

We have now identified a region on the cluster-w4 antigen against which it is possible to generate antibodies which advantageously have a higher binding affinity for the cluster-w4 antigen than leukocyte CD24 antigen. The site we have identified is that around and including the valine mutation at position 57 of the cluster-w4 polypeptide chain. Until our experiments there has been no suggestion that this mutation is presented on the surface of small cell lung carcinoma cells and that it can be serologically defined.

Thus, according to one aspect of the invention, we provide a human small cell lung carcinoma cell binding agent which selectively binds to the cluster-w4 polypeptide of said carcinoma cell at a binding site located at and around valine-57 of the cluster-w4 polypeptide.

The position of the binding site is defined herein by reference to the numbering of the amino acid sequence obtainable by expression of the cDNA coding for the cluster-w4 polypeptide as described by Jackson, D., et al in Cancer Res. ibid.

The binding site located at and around valine-57 comprises at least the valine-57 amino acid, but apart from this essential element may be of variable size and composition. Thus, for example, the binding site may comprise at least the tripeptide sequences K-$V^{57}$-A, T-K-$V^{57}$ or $V^{57}$-A-G (where each letter represents the internationally recognised one-letter symbol for an amino acid and $V^{57}$ represents valine at position 57 of the cDNA-encoded cluster-w4 polypeptide) or longer sequences selected from $(A)_m$-$(T)_n$-$(T)_o$-$(K)_p$-$V^{57}$-$(A)_q$-$(G)_r$-$(G)_s$-$(A)_t$ (SEQ ID NO:2) (where the subscripts m to t inclusive may be the same or different and is each zero or the integer 1), provided that one of the core sequences K-V-A, T-K-V or V-A-G is present.

The term "selectively binds" as used herein in relation to the binding agent according to the invention means that the agent has no useful binding affinity for locations in the cluster-w4 polypeptide outside of the binding site located at and around valine-57 and, importantly, does not cross-react in vivo with normal human tissue in such a way to limit its usefulness. In this latter respect, the binding agent according to the invention preferably has no useful binding affinity for the CD24 antigen of normal human B-cells. In general, the term "useful binding affinity" is intended to mean a binding affinity of $10^{-8}$M or less In particular, the binding agent according to the invention will have a binding affinity for the $V^{57}$ binding site of at least about $10^{-8}$M, especially in the range $10^{-8}$–$10^{-12}$M, while having little binding affinity for example $10^{-7}$M or higher, for other locations in the cluster-w4 polypeptide or the CD24 antigen.

In one preference, the binding agent according to the invention has a binding affinity for the $V^{57}$ binding site of the cluster-w4 polypeptide of human SCLC cells and a binding affinity for the CD24 polypeptide of normal human B cells in a molar concentration ratio of 20 or higher, especially 30 or higher.

Binding agents which meet the above selectivity criteria may be identified using the cluster-w4 and CD24 peptides described above in conventional peptide binding assays, for example as described by Weber et al ibid, and by standard cell binding assays, for example as described by Krause, D et al in Behring Inst. Mitt., No. 87, 56–67 (1990), and in the Examples hereinafter.

The binding agent according to the invention can be any proteinaceous material which contains one or more amino acid sequences which confer the selective cluster-w4 polypeptide binding capability, or any other naturallyoccurring or synthetic proteinaceous or other material which is capable of mimicking the action of this sequence or sequences.

The binding agent in this, and other aspects of the invention, is preferably an antibody. As used herein the term antibody is to be understood to mean a whole antibody or a fragment thereof, for example a F(ab)$_2$, Fab, Fv, V$_H$ or V$_K$ fragment, a single-chain antibody, e.g. a single-chain F$_v$ fragment, a multimeric monospecific antibody or fragment thereof, or a bi- or multispecific antibody or fragment thereof.

The antibody according to the invention may be a polyclonal or, especially, a monoclonal antibody. The antibody may belong to any immunoglobulin class, and may be for example an IgG, for example IgG$_1$, IgG$_2$, IgG$_3$, IgG$_4$, IgE, IgM or IgA antibody. It may be of animal, for example mammalian origin, and may be for example a murine, rat or human antibody. Alternatively, the antibody may be a chimeric antibody. The term chimeric antibody is used herein to mean any antibody containing portions derived from different animal species. Particular examples include those antibodies having a variable region derived from a murine, rat or other antibody and a human immunoglobulin constant region, and those antibodies in which one or more complementarily determining region [CDR] sequences and optionally one or more variable region framework amino acids are derived from a murine, rat or other antibody and the remaining portions of the variable and the constant regions are derived from a human immunoglobulin.

The binding agents according to the invention are of use in the diagnosis and therapy of small cell lung carcinoma in man and such uses form a further aspect of the invention.

For use in diagnosis or therapy the binding agent may be formulated in conventional manner, and the invention therefore extends to a pharmaceutical composition comprising a small cell lung carcinoma cell binding agent which selectively binds to the cluster-w4 polypeptide of said carcinoma cell at a binding site located at and around valine-57 of the cluster-w4 polypeptide, together with one or more pharmaceutically acceptable diluents, carriers or excipients.

The composition according to the invention may take any form suitable for administration to the human body. Thus, for example, where the binding agent is a protein such as an antibody the pharmaceutical composition may be in liquid form, for example a solution of the protein in a sterile physiologically acceptable buffer, for administration by for example an intravenous, intraperitoneal or intramuscular route.

For therapeutic or diagnostic uses the binding agent according to the invention will generally be administered in a pharmaceutically effective amount. The exact dose to be administered will vary according to the intended use of the binding agent and on the age and condition of the patient, but, for example, where the binding agent is an antibody, may be typically varied from about 0.1 mg to 1000 mg, for example from about 1 mg to 500 mg. The binding agent may be administered as a single dose, or in a continuous manner over a period of time. Doses may be repeated as appropriate.

Where the binding agent according to the invention is an antibody which has a Fc region capable of initiating pathways and mechanisms naturally available in the body to inhibit the growth of tumour cells, such as complement lysis and antibody dependent cellular cytotoxicity, then this may be used directly in therapy. Alternatively, for use in therapy and diagnosis, the binding agent may have linked to it an effector or reporter molecule.

Thus, according to a further aspect of the invention, we provide a conjugate molecule comprising a human small cell lung carcinoma cell binding agent which selectively binds to the cluster-w4 polypeptide of said carcinoma cell at a binding site located at and around valine-57 of the cluster-w4 polypeptide, and is linked to an effector or reporter molecule. Such conjugates may be formulated for use in the diagnosis or therapy of small cell lung carcinoma in man as described above and the invention is to be understood to extend to such uses of, and to pharmaceutical compositions containing, the conjugates.

In the conjugates according to the invention, the term "effector molecule" is to be understood to mean any group capable of eliciting a change in, or a response from, a biological system and which also confers this property to the conjugate. The term "reporter molecule" is to be understood to mean any group which is detectable by analytical means in vitro and/or in vivo and which confers this property to the conjugate. Where desired the effector or reporter molecule may be in the form of an inactive precursor, for subsequent activation in vivo at the target site, or may be contained in a carrier material for subsequent release at the target site.

Effector molecules include, for example, antineoplastic agents, toxins (such as enzymatically active toxins of bacterial or plant origin and fragments thereof e.g. ricin and fragments thereof) biologically active proteins, for example enzymes, nucleic acids and fragments thereof, e.g. DNA, RNA and fragments thereof, radionuclides, particularly radioiodide, and chelated metals.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphoramide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperamicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Particularly useful effector groups are calichaemicin and derivatives thereof (see for example South African Patent Specifications Nos. 85/8794, 88/8127 and 90/2839).

Chelated metals include chelates of di-or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferrioxamine and derivatives thereof.

Suitable reporter groups include chelated metals, fluorescent compounds or compounds which may be detected by NMR or ESR spectroscopy.

The binding agents according to the invention may in general be identified and/or prepared using a peptide or a derivative thereof comprising an amino acid sequence corresponding to the binding site sequence at and around valine-57 of the cluster-w4 polypeptide as the starting point. The invention therefore extends to the use of such a peptide or a derivative thereof in the preparation of a binding agent which selectively binds to the cluster-w4 polypeptide of human small cell lung carcinoma.

The peptide for use in this aspect of the invention may in general be a tripeptide or longer molecule as described above in relation to the binding site. Thus, for example, the peptide may be selected from $(A)_m$-$(T)_n$-$(T)_o$-$(K)_p$-V-$(A)_q$-$(G)_r$-$(G)_s$-$(A)_t$-$(L)_u$ (SEQ ID NO:1) where m-t are as defined previously and u is zero or the integer 1, provided of course that at least one of the core sequences K-V-A, T-K-V or V-A-G is present, and derivatives thereof. Derivatives include longer peptides incorporating this sequence together with one, two or three extra amino acids, for example at one or both ends of the sequence. Such extra amino acids may be added, for example to facilitate linkage of the peptide to a solid support or carrier. Alternatively certain amino acids may be substituted for others in the above sequence where this amounts to a conservative change, providing of course that the desired selectivity as defined herein is obtained. Derivatives of peptides for use in this aspect of the invention also include for example peptides in which one or more functional groups, such as the N-terminal amino, C-terminal carboxyl or a reactive group on an amino acid side chain have been blocked or protected, for example by carbonylation, amidation or other reaction, and/or in which one or more amino acids is labelled by a detectable group, for example by a fluorescent group, a radiolabel or a group detectable by NMR or ESR spectroscopy.

The peptide or a derivative thereof may be employed, using conventional techniques, for screening to obtain a binding agent according to the invention. Alternatively, and in particular, the peptide or a derivative thereof may be used, either alone, or coupled to an immunogenic carrier, as an immunogen to generate antibodies according to the invention. Immunogens comprising a peptide $(A)_m$-$(T)_n$-$(T)_o$-$(K)_p$-V-$(A)_q$-$(G)_r$-$(G)_s$-$(A)_t$-$(L)_u$ (SEQ ID NO:1) (as defined herein) or a derivative thereof linked to an immunogenic carrier are new and form a further aspect of the invention.

For use in this aspect according to the invention the peptide may be prepared from appropriately activated and/or protected amino acids using routine peptide synthesis techniques, [see for example Merrifield, B, Science (1985), 232, 341–347]. For use as an immunogen, the peptide or a reactive derivative thereof may be linked to an immunogenic carrier, such as another protein, e.g. keyhole limpet hemocyanin or cationised bovine serum albumin, or a polypeptide such as polylysine, using conventional techniques, for example standard multiple antigenic peptide (MAP) procedures.

Antibodies according to the invention may be prepared by conventional immunisation and recombinant DNA techniques. Thus, for example polyclonal antibodies may be obtained from the sera of animals immunised with a peptide immunogen as just described. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived from the spleen cells of an animal e.g. a mouse or rat immunised as just discussed and fused to an appropriate "immortal" B-tumour cell for example a Sp2/0 cell. In each instance, the antibody may be recovered from either the serum or the hybridoma by making use of standard purification and/or concentration techniques, for example by chromatography, using for example Protein A or by other affinity chromatography employing a peptide as described above.

Once a cell line, for example a hybridoma, expressing an antibody according to the invention has been obtained it is possible to clone therefrom the cDNA and to identify the variable region genes encoding the desired antibody, including the sequences encoding the CDRs. From here, other chimeric antibodies according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g. a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

Where it is desired to obtain a conjugate according to the invention this may be prepared by standard chemical or recombinant DNA procedures in which the binding agent is linked either directly or via a coupling agent to the effector or reporter molecule. Particular chemical procedures include for example those described in International Patent Specification Nos. WO 93/06231, WO 92/22583, WO 90,09195 and WO 89/01476. Alternatively, and particularly where the binding agent and effector or reporter molecule is a protein or polypeptide the conjugate may be prepared using recombinant DNA procedures, for example as described in International Patent Specification No. WO 86/01533 and European Patent Specification No.392745.

Peptides as defined herein having an amino acid sequence corresponding to the binding site sequence at and around valine-57 of the cluster-w4 polypeptide may have further uses in the diagnosis and therapy of small cell lung carcinoma and the invention is to be understood to extend to such compounds for such uses. Thus, for example, in one use the peptides $(A)_m$-$(T)_n$-$(T)_o$-$(K)_p$-V-$(A)_q$-$(G)_r$-$(G)_s$-$(A)_t$-$(L)_u$ (SEQ ID NO:1) and derivatives thereof as described above may form a reagent for a diagnostic test for human small cell lung carcinoma, essentially to determine whether antibodies specific for the peptides, and therefore for the tumour, are present in a patient. The test may be generally carried out by contacting body fluid from the patient with a peptide or a derivative thereof and detecting any complexed material.

In a second use, a peptide $(A)_m$-$(T)_n$-$(T)_o$-$(K)_p$-V-$(A)_q$-$(G)_r$-$(G)_s$-$(A)_t$-$(L)_u$ (SEQ ID NO:1) or a derivative thereof may be used as an immunostimulant in patients with small cell lung carcinoma, to stimulate the natural immune response against the tumour. For use in this aspect of the invention the peptide may be formulated in conventional manner as a pharmaceutical composition, for example, as described above in relation to the binding agents of the invention, optionally together with a pharmaceutically acceptable adjuvant or carrier, and the invention is to be understood to also extend to such a composition. The composition may be administered by any suitable route, for example by an intravenous, intraperitoneal or intramuscular route, in single or repeat doses as necessary.

The following Examples illustrates the invention. In the Examples, reference is made to the accompanying Figures in which:

EXAMPLE 1

The multiple antigenic peptide (MAP):

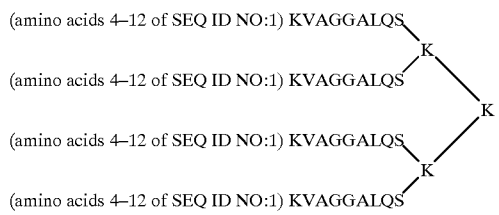

(amino acids 4–12 of SEQ ID NO:1) KVAGGALQS
(amino acids 4–12 of SEQ ID NO:1) KVAGGALQS
(amino acids 4–12 of SEQ ID NO:1) KVAGGALQS
(amino acids 4–12 of SEQ ID NO:1) KVAGGALQS was prepared by peptide synthesis using appropriately protected amino acid starting materials and then used to immunise BALB/c mice (3 injections i/p at fortnightly intervals). Sera from individual mice were then analysed by FACScan for binding of antibodies to the human small cell lung carcinoma cell line H69, (known to carry the cDNA T/C mutation and therefore expected to express valine at position 57 of the cluster-w4 polypeptide) and the human erythroleukemic cell line K562 (previously used to clone normal human CD24 and known to express only alanine at position 57). Both cell lines were obtained from the American Type Culture Collection (Rockville, Md., USA). The results of the FACScan analysis are shown in FIG. 1 which clearly exemplifies the differential binding of antibodies in sera from mice 25 and 30 to the SCLC cell line H69 but not to the erythroleukemic line K562. These results demonstrate that mice 25 and 30 have antibodies capable of binding the mutant KVA sequence of the cluster-w4 polypeptide, and distinguishing this sequence from the KAA normal sequence. In general they demonstrate that the valine mutant is presented and is accessible on SCLC cell surfaces, and can be serologically defined.

EXAMPLE 2

Generation of Monoclonal Antibodies to the Cluster-w4 Polypeptide of Small Cell Lung Carcinoma Cells Female LOU rats were immunised with three intraperitoneal injections of peptide C-S-N-A-T-T-K-V-A-G-$NH_2$ (SEQ ID NO:4) coupled to keyhole limpet hemocyanin [KLH], given at fortnightly intervals in adjuvant. Four days before fusion a further boost of 50 μg KLH-C-S-N-A-T-T-K-V-A-G (SEQ ID NO:4) was given i/p.

Spleen cells from one rat which exhibited the highest titer on H69 cells were fused to mouse Sp2/0 partners and the fusion plated out into 960 wells.

In the primary screen, hybridoma supernatants were incubated on ELISA plates coated with peptide C-S-N-A-T-T-K-V-A-G (SEQ ID NO:4), and the presence of rat IgG was revealed with a horseradish peroxidase conjugated goat anti-rat Fc antibody. From this assay 120/960 wells gave positive binding. These supernatants were taken through to a secondary screen in which binding to H69 cells was assessed by FACScan analysis. From this round of selection, 5 supernatants out of 120 were positive. Hybridomas from these 5 positive wells were cloned twice by limiting dilution and established cell lines developed. After screening on the SCLC cell lines H69 and H128, (obtained from the American Type Culture Collection, *ibid*), a cell line 9A6:3B4:6F3 was selected for further study.

Purification of Rat Monoclonal Antibody 9A6

The 9A6 hybridoma described above was grown in RPMI 1640 medium containing 1% fetal calf serum (FCS) and glutamine. After harvesting, the supernatant (2.3 liters) was sterile filtered through a 0.2 μm filter and concentrated 10-fold by ultrafiltration on a 10 kDa cut-off membrane. The 9A6 antibody was purified on a protein G-sepharose column (2.6 cm diameter×2.8 cm) which was run in 20 mM sodium phosphate, pH7.0. The sample was eluted by applying a 10 column volume gradient (0.15M $Na_2HPO_4$/0.1M citric acid) and antibody containing fractions were pooled and neutralised by addition to 2M Tris/HCl to pH6.

Contaminating bovine IgG was removed by applying the sample (10 mg aliquots) to an anti-bovine IgG-sepharose column (1.6 cm diameter×9 cm) equilibrated with 20 mM sodium phosphate pH7.0. The flow-through fractions (containing purified 9A6) were pooled and the column was regenerated in 1M guanidine HCl/1M $MgCl_2$/1M KCl/10 mM Tris-HCl, pH8 and re-equilibrated in 20 mM sodium phosphate pH7.0 before re-use. The pooled 9A6 fractions were then concentrated in an Amicon stirred cell fitted with a 10 kDa membrane. The purified antibody was then sterile-filtered before use.

Fluoresceination of Rat Monoclonal Antibody 9A6 and Affinity Determinations

The antibody 9A6 was labelled with FITC according to the method of Wood et al [J. Immuno. 95, 225 (1965)].

The antibody (1 ml) was buffer-exchanged using a PD-10 column to give 1 ml of 9A6 at 3.5 mg/ml. Fluorescein isothiocyanate (FITC, 7 μl, 10 mg/ml in dimethylsulphoxide) was added and the mixture incubated at room temperature for 135 min. The FlTC/antibody ratio was determined to be 1.1 according to the following equation:

$$[\text{Antibody}, \mu M] = ((A280 - (0.36 \times A495))/1.4)/0.21$$

$$[\text{FITC}, \mu M] = \frac{A495}{0.077}$$

$$\text{FITC} / \text{Antibody} = [\text{FITC}, \mu M] / [\text{Antibody}, \mu M]$$

Affinity determinations were carried out essentially as described by Krause et al *ibid*. The FITC-9A6 was diluted in phosphate-buffered saline/5%FCS/0.1% (w/v) sodium azide buffer, pH7.2 in the concentration range 3-0.07 μg/ml and incubated for 1 h on ice with 100,000 cells per tube. The fluorescence intensity of the cells was measured by FACScan and the calculations were performed according to the method of Krause et al. The fluorescence was calibrated using standard beads (Flow Cytometry Standards Corporation).

Figure 2:
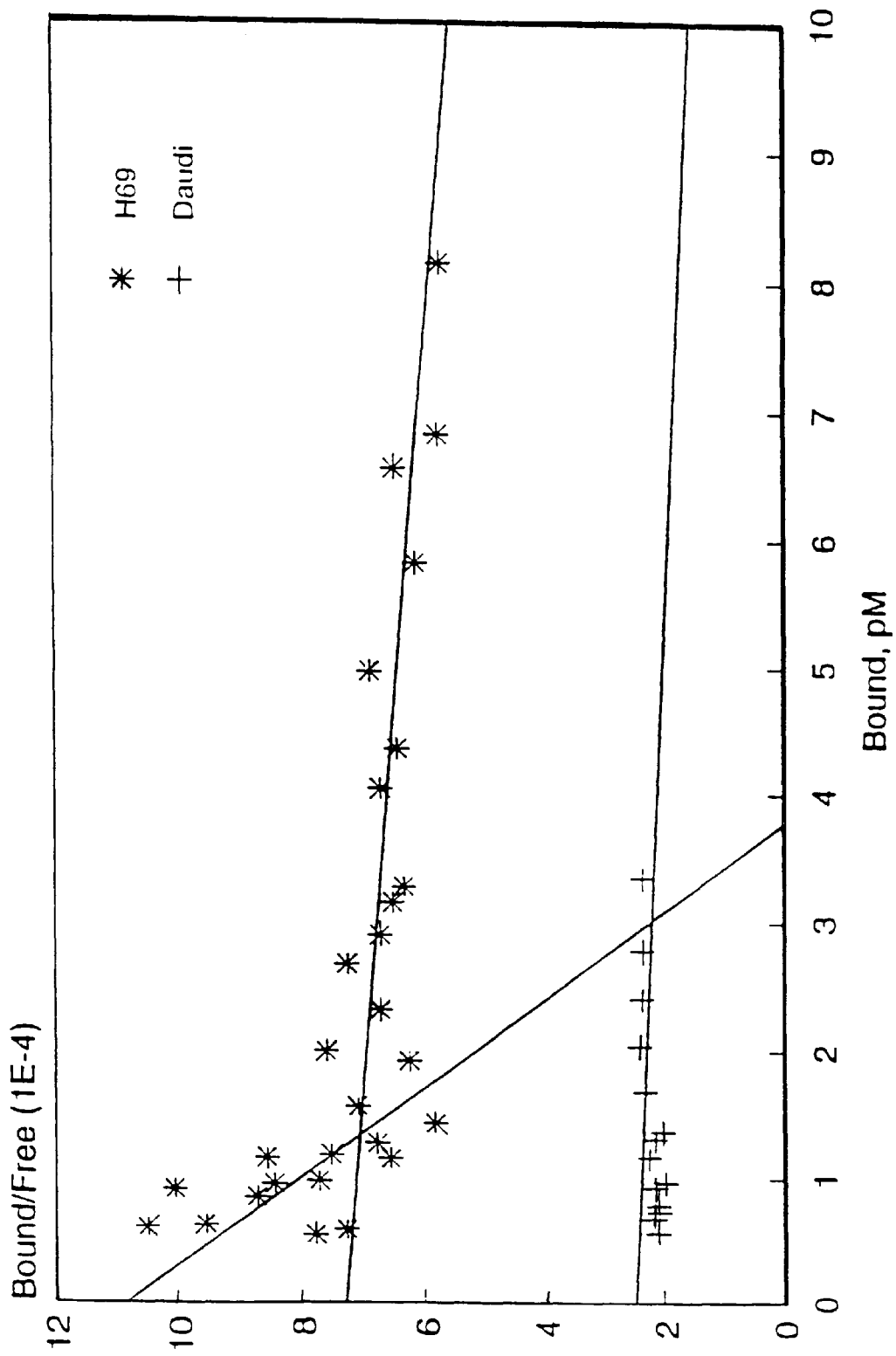
FIG. 2 is a Scatchard Plot showing the binding of rat monoclonal antibody 9A6 to the human small cell lung carcinoma cell line H69 and to the human erythroleukemic cell line, Daudi.

FIG. 2 shows a Scatchard Plat where the binding of fluorescein labelled 9A6 to the SCLC cell line H69 is compared to the binding to the human erythroleukemia B cell line, Daudi. Daudi cells have been shown to produce mRNA coding only for alanine at position 57 (Jackson et al.,*ibid*) and would not be expected to express mutant CD24 (the cluster-w4 polypeptide) with valine at this position.

9A6 bound both H69 and Daudi cell lines with low affinity (100 nM and 120 nM respectively) revealing 180, 000 sites on H69 cells and 70,000 sites on Daudi cells. High affinity binding sites (4 nM and 9,000 sites/cell) were revealed only on H69 cells with 9A6. No such binding could be demonstrated with Daudi cells.

FIG. 3 shows a Scatchard Plot in which 9A6 is shown to bind another SCLC cell line H128 with both high affinity (3.4 nM; 5,000 sites/cell) and low affinity (120 nM; 100,000 sites/cell).

SUMMARY

Using an immunisation protocol with a peptide sequence corresponding to that spanning valine at position 57 of the cluster-w4 polypeptide of SCLC cells, a rat monoclonal antibody 9A6:3B4:6F3 has been produced. This antibody shows high affinity binding (3–4 nM) to human SCLC cell lines H69 and H128 which is not demonstrable on the human non-cancerous erythroleukemia B cell line Daudi.

Behaviour of Rat Monoclonal Antibody 9A6 in SCLC Tissue

In a further series of binding experiments using labelled antibody 9A6, it has been demonstrated that in addition to binding to SCLC cell lines the antibody also binds to human small cell lung carcinoma tissue, thus providing further support for the potential use of such an antibody in the diagnosis and/or treatment of SCLC.

I claim:

1. An antibody which binds to an epitope of the cluster-w4 polypeptide of a human small cell lung carcinoma cell, wherein said epitope includes amino acid residue valine-57.

2. An antibody according to claim 1 which has a binding affinity at a binding site which includes valine-57 of the cluster-w4 polypeptide in the range of $10^{-8}$–$10^{-12}$M and a binding affinity of $10^{-7}$M or higher for other locations in the cluster-w4 polypeptide or the CD24 antigen of normal human B cells.

3. A pharmaceutical composition comprising an antibody according to claim 1, together with one or more pharmaceutically acceptable diluents, carriers or excipients.

4. An antibody according to claim 1, wherein said epitope includes one or more of the amino acid sequences T-K-$V^{57}$, K-$V^{57}$-A or $V^{57}$-A-G.

5. An antibody according to claim 1 or claim 4, linked to an effector or reporter molecule.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens
<220> FEATURE:
<221> NAME/KEY: VARIANT
<222> LOCATION: (1)..(4)
<223> OTHER INFORMATION: Xaa at Position 1  is either Ala or none;
      Xaa at Position 2 is either Thr or none;  Xaa at Position
      3  is either Thr or none;  Xaa at Position  4  is
      either Lys or none.
<220> FEATURE:
<221> NAME/KEY: VARIANT
<222> LOCATION: (6)..(10)
<223> OTHER INFORMATION: Xaa (Position 6) is either Ala or none; Xaa
      (Position 7) is either Gly or none; Xaa (Position
      8) is either Gly or none; Xaa (Position 9) is
      either Ala or none; Xaa (Position 10) is either
      Leu or none
<220> FEATURE:
<221> NAME/KEY: VARIANT
<222> LOCATION: (1)..(10)
<223> OTHER INFORMATION: At least one of the core sequences
      Lys-Val-Ala, Thr-Lys-Val, or Val-Ala-Gly is present.

<400> SEQUENCE: 1

Xaa Xaa Xaa Xaa Val Xaa Xaa Xaa Xaa Xaa
 1               5                  10

<210> SEQ ID NO 2
<211> LENGTH: 9
<212> TYPE: PRT
<213> ORGANISM: Homo sapiens
<220> FEATURE:
<221> NAME/KEY: VARIANT
```

```
<222> LOCATION: (1)..(4)
<223> OTHER INFORMATION: Xaa at Position 1  is either Ala or none;
      Xaa at Position 2 is either Thr or none;  Xaa at Position
      3  is either Thr or none;  Xaa at Position  4  is
      either Lys or none.
<220> FEATURE:
<221> NAME/KEY: VARIANT
<222> LOCATION: (6)..(9)
<223> OTHER INFORMATION: Xaa at Position 6 is either Ala or none;
      Xaa at Position 7 is either Gly or none;  Xaa  at
      Position 8 is either Gly or none;  Xaa at Position
      9 is either Ala or none
<220> FEATURE:
<221> NAME/KEY: VARIANT
<222> LOCATION: (1)..(9)
<223> OTHER INFORMATION: At least one of the core sequences Lys-Val-Ala,
      Thr-Lys-Val, or Val-Ala-Gly is present

<400> SEQUENCE: 2

Xaa Xaa Xaa Xaa Val Xaa Xaa Xaa Xaa
 1               5

<210> SEQ ID NO 3
<211> LENGTH: 14
<212> TYPE: PRT
<213> ORGANISM: Homo sapiens

<400> SEQUENCE: 3

Ala Thr Thr Lys Val Ala Gly Gly Ala Leu Gln Ser Thr Ala
 1               5                  10

<210> SEQ ID NO 4
<211> LENGTH: 10
<212> TYPE: PRT
<213> ORGANISM: Homo sapiens

<400> SEQUENCE: 4

Gly Ala Val Lys Thr Thr Ala Asn Ser Cys
 1               5                  10
```